United States Patent [19]

Fiehler

[11] Patent Number: 5,454,958
[45] Date of Patent: * Oct. 3, 1995

[54] METHOD FOR SAMPLING IN A CONTAINER HAVING A MATERIAL THEREIN WHICH SEPARATES FROM A BARRIER MATERIAL

[75] Inventor: William R. Fiehler, St. Louis, Mo.

[73] Assignee: Sherwood Medical Company, St. Louis, Mo.

[ * ] Notice: The portion of the term of this patent subsequent to Aug. 17, 2010 has been disclaimed.

[21] Appl. No.: 115,403

[22] Filed: Sep. 1, 1993

Related U.S. Application Data

[60] Division of Ser. No. 808,312, Dec. 16, 1991, Pat. No. 5,269,927, which is a continuation-in-part of Ser. No. 706,916, May 29, 1991, Pat. No. 5,236,604.

[51] Int. Cl.⁶ .................................................... B01D 21/26
[52] U.S. Cl. .......................... 210/782; 210/516; 210/787; 210/789; 422/101; 422/102; 436/177
[58] Field of Search .................... 210/513, 514, 210/515, 516, 782, 787, 789; 422/72, 73, 101, 102; 436/177

[56] References Cited

U.S. PATENT DOCUMENTS

| | | | |
|---|---|---|---|
| 3,780,935 | 12/1973 | Lukacs et al. | 210/516 |
| 3,909,419 | 9/1975 | Ayres | 210/518 |
| 3,919,085 | 11/1975 | Ayres | 210/516 |
| 3,920,549 | 11/1975 | Gigliello et al. | 210/516 |
| 3,920,557 | 11/1975 | Ayres | 210/516 |
| 3,972,812 | 8/1976 | Gresl, Jr. | 210/359 |
| 3,981,804 | 9/1976 | Gigliello | 210/516 |
| 4,021,340 | 5/1977 | Zine, Jr. | 210/515 |
| 4,046,699 | 9/1977 | Zine, Jr. | 10/516 |
| 4,055,501 | 10/1977 | Cornell | 210/516 |
| 4,088,582 | 5/1978 | Murty et al. | 210/516 |
| 4,101,422 | 7/1978 | Lamont et al. | 210/516 |
| 4,148,764 | 4/1979 | Lamont et al. | 210/516 |
| 4,235,725 | 11/1980 | Semersky | 210/516 |
| 4,246,123 | 1/1981 | Cornell et al. | 210/782 |
| 4,310,430 | 1/1982 | Ichikawa et al. | 210/789 |
| 4,350,593 | 9/1982 | Kessler | 210/516 |
| 4,386,003 | 5/1983 | Fiehler | 210/516 |
| 4,426,290 | 1/1984 | Ichikawa et al. | 210/516 |
| 4,569,764 | 2/1986 | Satchell | 210/511 |
| 4,816,168 | 3/1989 | Carrol et al. | 210/782 |
| 4,818,418 | 4/1989 | Saunders | 210/782 |
| 4,844,818 | 7/1989 | Smith | 210/789 |
| 4,867,887 | 9/1989 | Smith | 210/782 |
| 4,946,601 | 8/1990 | Fiehler | 210/782 |
| 4,957,637 | 9/1990 | Cornell | 219/782 |
| 5,019,243 | 5/1991 | McEwen et al. | 210/516 |
| 5,030,341 | 7/1991 | McEwen et al. | 210/516 |
| 5,053,134 | 10/1991 | Luderer et al. | 210/516 |
| 5,213,765 | 5/1993 | Kasai et al. | 422/101 |
| 5,236,604 | 8/1993 | Fiehler | 210/516 |
| 5,269,927 | 12/1993 | Fiehler | 210/516 |

*Primary Examiner*—John Kim
*Attorney, Agent, or Firm*—Andrew J. Beck; Montgomery W. Smith; Richard D. Allison

[57] ABSTRACT

A process and method for preventing a separated material from interfering with the portion of a fluid to be sampled for use in a serum or plasma collection device including a gel material for partitioning and separating heavier and lighter phases of a fluid sample such as a blood sample. The device preferably includes a member such as a disc-shaped or ring-shaped member or a combination thereof to prevent the separated material from interfering with the sampling of the separated fluid sample. The member is preferably formed of hydrophobic and/or non-wetted material and has a specific gravity different from the specific gravity of the lighter phase. The process may also include a member which physically separates the separated material from the fluid to be sampled to allow the user to obtain an uncontaminated fluid sample.

14 Claims, 6 Drawing Sheets

METHOD FOR SAMPLING IN A CONTAINER HAVING A MATERIAL THEREIN WHICH SEPARATES FROM A BARRIER MATERIAL

This is a divisional of copending patent application Ser. No. 07/808,312 filed on Dec. 16, 1991, U.S. Pat. No. 5,269,927, which is a continuation-in-part of U.S. Ser. No. 07/706,916 filed on May 29, 1991, now U.S. Pat. No. 5,236,604.

FIELD OF THE INVENTION

This invention relates to blood serum separator tubes useful for separating the serum and red blood cell portions of a collected blood sample after centrifugation. More specifically, the invention relates to a device for improving the performance of the gel materials which are used as partitioning agents in serum or plasma separator tubes.

BRIEF DESCRIPTION OF THE PRIOR ART

Blood collection and separating devices are disclosed in a number of prior patents. In these devices, a blood sample is added to a collection tube containing a gel-like or barrier material having a density between that of the blood serum and red blood cells. During centrifugation, the gel material acts as a barrier or partitioning agent and is displaced upwardly in the blood sample until it reaches an equilibrium location between the lighter blood serum or plasma and the heavier coagulum or red blood cell portions of the blood sample. At equilibrium, the gel material forms a mechanical barrier between the serum and the coagulum. The lighter serum portion can then be either decanted directly from the collection tube or sampled using automated blood analyzing equipment.

The specific gravity of the blood serum or plasma portion of the blood sample is between approximately 1.026 and 1.031, and the specific gravity of the coagulum portion of the blood sample is between approximately 1.092 and 1.095. Therefore, the specific gravity of the gel material is preferably between about 1.03 and 1.09 and preferably about 1.04 so that once the blood sample is centrifuged, the gel material will form a barrier between the serum and the coagulum. A preferred gel material is a thixotropic composition which is described in the inventor's own prior U.S. Pat. No. 4,386,003, entitled "Blood Separating Composition," the entire disclosure of which is hereby incorporated by reference. As described therein, a preferred thixotropic gel material is a silica-silicone fluid gel formed by the reaction between silicone fluid, a filler material (such as silica particles) had a thixotropic property-imparting amount of a network former. The relative amounts of the gel components are selected so as to yield a gel having a specific gravity between about 1.03 and 1.09, and preferably about 1.04. The silicone fluids used to prepare such gels are conveniently characterized as "silicone oils" and the terms "silicone fluid" and "silicone oil" are used herein interchangeably.

Additionally, the use of hydrocarbon-based gel materials are also known. Such hydrocarbon-based gel materials include polyester, disclosed in Kessler et. al., U.S. Pat. No. 4,350,593, entitled "Assembly, Compositions and Method for Separating Blood"; copolyesters, disclosed in Lamont et al., U.S. Pat. No. 4,101,422, entitled "Copolyesters Useful In Blood Separation Assemblies" and also in Lamont, U.S. Pat. No. 4,148,764, entitled "Copolyesters Useful In Blood Separation Assemblies"; polybutene, disclosed in Zine, Jr., U.S. Pat. No. 4,021,340, entitled "Blood Separating Composition"; polybutadiene, disclosed in Semersky, U.S. Pat. No. 4,235,725, entitled "Sterile Blood-Collecting And Separating Device"; and alpha-olefin-dimaleate copolymer, disclosed in Ichikawa et al., U.S. Pat. No. 4,426,290, entitled "Apparatus For Separating Blood." Additionally, U.S. Pat. No. 4,055,501 entitled "Fluid Collection Device With Phase Partitioning Means," granted to Cornell also discloses the use of hydrocarbon-based materials including polybutene and polybutadiene.

One problem which may be encountered with the use of the foregoing gel materials is that silicone oil or other gel materials may separate during storage of the collection tube. The separated material may cause sampling errors or other sampling difficulties with as little as 10% or 20% of the top surface of the serum portion being covered by the separated material. This generally means that as little as about 5 microliters of separated material may adversely affect the sampling of a blood 'sample. For convenience and clarity, the separated silicone oil from the thixotropic gel materials and the separated materials from the hydrocarbon-based gel materials will be generally referred to interchangeably hereinafter as the separated "oil" or "degradation material". The degradation material or oil which separates from the gel material is believed to be, at least partially, a function of the exposed surface area of the gel material in the collection tube. Additionally, the rate of degradation Of the gel material may be increased by improper storage of the collection tube, i.e., storing the collection tube on its side or subjecting the blood collection tube to extreme or varied temperatures.

In another of inventor's prior patents, U.S. Pat. No. 4,946,601, one approach to solve the problem of oil separation from a thixotropic gel material is disclosed. This patent is incorporated herein by reference and discloses the use of a separately curable gel layer which is positioned between the thixotropic gel material and the atmosphere contained in the collection tube. The use of this additional gel layer is designed to prevent separation of the silicone oil from the silica-silicone fluid gel material prior to use. Additionally, this patent discloses the micro-encapsulation of the thixotropic gel material in a number of capsules to prevent exposure of the thixotropic gel material to the atmosphere contained within the collection tube.

The separated oil from the gel materials are typically lighter in density than the formed gel barrier and therefore, these separated materials rise into or on top of the separated serum portion of the blood sample. The presence of the relatively small amount of separated oil in or on the top of the separated serum portion may cause sampling errors or disable the probe of an automated clinical chemistry sampling instrument. These instruments are being utilized with greater frequency due to the ability of the instrument to rapidly perform a variety of tests on a single blood sample while minimizing the exposure of the laboratory personnel to potentially contaminated blood samples. In many of these instruments the probe member is automatically lowered into the center of the collection tube until the probe member contacts the serum sample.

In one such device, an electrical current is created on the probe member so that when the serum sample is contacted, the electrical current passes through the serum sample and further downward movement of the probe member is discontinued. In another such instrument, an air pressure gradient is created at the distal end of the probe member so that once the serum sample is contacted by the probe member, the air pressure gradient changes and the downward movement of the probe member into the collection tube is discontinued. If the top surface of the serum sample includes separated oil, the automatic lowering of the probe member in both of these instruments may be adversely affected. For example, if the electrical probe member contacts the separated oil on the surface of the serum sample, the separated oil may coat the distal end of the probe member and the probe member will not detect contact with the serum sample. This may cause the probe member to enter the gel material, obtain an improper sample or indicate that a sampling error has occurred. In the instrument that utilizes an air pressure gradient to detect contact with the serum portion of the blood sample, the probe member will stop at the layer of separated oil on the top surface of the serum sample and the separated oil may be drawn into the sampling instrument when the serum sample is drawn into the probe member. If this occurs, the results of the tests preformed by the instrument may be inaccurate due to the presence of the separated oil or the separated oil may, in certain instances, cause damage to the probe member or instrument.

During testing of collection tubes having visually observable oil separation, it has been observed that during centrifugation, the separated oil travels upwardly from the bottom of the collection tube along the sides of the collection tube generally in the same manner as the gel material, travels upwardly along the sides of the collection tube. As the centrifugation continues, the gel material will accumulate at the interphase of the lighter serum and the heavier coagulum. The separated oil will continue to travel upwardly along the sides of the collection tube until it reaches the top of the serum portion. The separated oil will then travel inwardly towards the center of the collection tube where it forms a top layer of separated oil positioned above the serum portion of the blood sample. Because the probe member of the automated sampling instrument is centrally positioned in the collection tube, whenever the separated oil has formed a layer above the serum portion of the blood sample, the probe will contact the separated oil prior to reaching the serum portion of the blood sample. Therefore, it is important that the separated oil either be removed from the center of the top surface of the serum portion or removed from the serum portion entirely.

In the past, it has been recommended that the technician touch the oil layer with either an applicator stick or pipette tip to remove the separated oil from the serum portion of the blood sample prior to placing the collection tube in the auto-sampling instrument. This is inconvenient due to the additional work required to be performed by the technician and the potential for the exposure of the technician to the blood sample either in the collection tube or on the applicator or pipette tip.

Therefore, a need remains for a convenient method of removing separated oil from the serum portion of the blood sample prior to the placement of the collection tube in the auto-sampling instrument and for an improved blood serum separating tube or plasma separation tube having the benefits without the drawbacks of the various commercially available serum separation blood collection tubes.

SUMMARY OF THE INVENTION

It is a broad object of the present invention to provide a blood serum separator tube or a plasma separator tube which conveniently and effectively separates the blood serum or plasma from the coagulum of the blood sample upon centrifugation and wherein the separated oil does not interfere with the operation of automated blood sampling instruments.

Another object of the present invention is to provide a blood serum separator tube which prevents separated oil from interfering with the test results of the blood sample.

A further object of the present invention is to enable laboratories to obtain test samples from collection tubes having a large amount of separated oil therein particularly where these oil contaminated samples were previously discarded as being unusable.

At least one form of the present invention may include a method for preventing the separated material of a gel-like material from interfering with the sampling of a portion of a separated and partitioned portion of a fluid such as blood, wherein the fluid has a lighter phase and a heavier phase and the specific gravity of the lighter phase is less than the specific gravity of the heavier phase, the method including:

- inserting a fluid sample into a container having a bottom end and an open end with a stopper means positioned thereon and an affinity member and gel-like material contained therein and wherein the gel-like material in the container has a specific gravity between the specific gravities of the lighter phase and heavier phase, and the affinity member has a specific gravity less than the specific gravity of the gel-like material;
- centrifuging the container for a time sufficient to cause the heavier phase of the fluid to migrate to the bottom of the container; the lighter phase to migrate upwardly to a position above the gel-like material and heavier phase and the affinity member to migrate into the lighter phase and above the gel-like material to allow the separated material from the gel-like material to adhere to the affinity member;
- obtaining a sample of the lighter phase by inserting a probe member therein in a manner such that the affinity member prevents the separated material from interfering with the sampling of the fluid.

The present invention may also include a method for preventing the separated material of a barrier material from interfering with the sampling of a portion of a separated portion of a fluid such as blood wherein the fluid has at least a lighter phase and a heavier phase and the specific gravity of the lighter phase, the method including:

- inserting a fluid sample into a container having a bottom end and an open end with a stopper means thereon and a barrier material therein, wherein the barrier material has a specific gravity between the specific gravities of the heavier phase and the lighter phase;
- centrifuging the container to separate the heavier and lighter phases of the fluid sample such that the barrier material forms a mechanical barrier between the heavier and lighter phases; and
- inserting a device means into the container to physically separate the separated material from the lighter phase to enable a sample of the lighter phase to be obtained from the container which is not contaminated by the separated material.

At least one form of the present invention may further include a method for preventing the separated material of a barrier material from interfering with the sampling of a portion of a separated portion of a fluid such as blood, wherein the fluid has at least a lighter phase and a heavier phase, and the specific gravity of the heavier phase is greater than the specific gravity of the lighter phase, the method including:

- inserting a fluid sample into a container having a bottom end and an open end with a stopper means thereon and a device means and barrier material therein, wherein the barrier material has a specific gravity between the specific gravities of the heavier phase and the lighter phase, and the device means has a specific gravity less than the specific gravity of the barrier material;

centrifuging the container to separate the heavier and lighter phases of the fluid sample such that the barrier material forms a mechanical barrier between the heavier and lighter phases, and the device means physically separates the separated material from the lighter phase to enable a sample of the lighter phase to be obtained from the container which is not contaminated by the separated material.

The present invention broadly involves a variety of approaches which utilize an affinity means to attract the separated oil and prevent the interference of the separated oil with the sampling of the blood sample. In a preferred form of the invention, a disc member having a density greater than the serum portion of the blood sample is dropped into the collection tube after centrifugation. The disc member is preferably constructed of a hydrophobic and/or non-wetted material so that the hydrophobic separated oil adheres to the disc as the disc sinks to the top of the gel barrier formed by the gel material.

In a second form of the present invention, a disc-shaped member or a ring-shaped member is supplied with the gel material in the collection tube. In this embodiment, the disc member or ring member has a density less than that of the serum portion of the blood sample and is preferably constructed of a hydrophobic and/or a non-wetted material. During centrifugation of this form of the invention, the disc member or ring member rises through the blood sample to the top of the serum portion. Because the disc member or ring member is hydrophobic and/or non-wetted, the separated oil will adhere to the disc member or ring member. With the ring member of this embodiment, the oil collects along the sides of the collection tube and is trapped between the sides of the collection tube and the outer surface of the ring member to prevent the formation of a layer of separated oil along the center of the top layer of the serum portion. With the disc member of this embodiment, the separated oil adheres to the bottom surface of the disc member and, as the probe member is lowered into the serum portion of the blood sample, the disc member is pushed out of the way by the probe member and an oil free serum sample may be obtained.

The third embodiment of the present invention involves coating the inner walls of the separator tube with a hydrophobic and/or non-wetted material so that the separated oil adheres to the sides of the collection tube to prevent formation of an oil layer along the top surface of the serum portion of the blood sample.

Further embodiments of the present invention involve the use of a member having a ring-shaped member and either a disc-shaped member or a funnel-shaped member on the bottom surface thereof. These alternate embodiments preferably have a specific gravity less than that of the gel material or serum portion of the blood sample so that these members may be added to the collection tube either before or after the serum separator tube has been centrifuged. As will be described more fully below, the first of these members preferably consists of an upper ring-shaped portion and a lower disc-shaped portion. The second of these members consists of a lower funnel-shaped member and an upper ring-shaped member. A common feature of both of these members is that they inhibit the travel of the separated oil along the sides of the collection tube and also towards the center of the collection tube above the serum portion of the blood sample.

DETAILED DESCRIPTION OF THE PREFERRED EMBODIMENT

The present invention is described hereinafter in the context of the presently preferred use of the present invention which is described in a serum separation blood collection tube. It should be understood that the present invention may also be used in plasma separation tubes or in other collection tubes wherein the separation of a material from a composition may interfere with the accuracy of the test to be conducted or the operation of the sampling equipment.

Referring now to FIGS. 1–5, the presently preferred form of the present invention is shown. The serum separator blood collection tube is referred to herein generally as serum separator tube 10 and includes a collection tube 12 having a conventional stopper 14 contained on the open end thereof. As described previously, the serum separator tube. 10 preferably includes a silicone-based thixotropic gel 16 although the present invention has been found to work with various commercially available hydrocarbon-based gel materials of the type described previously. Additionally, the serum separator tube 10 may include an energizer (not shown) to increase the flow of the gel material 16 from the bottom of the collection tube 12 to form the gel layer during centrifugation. The disc member 18 of the present embodiment has a specific gravity greater than the specific gravity of the separated serum portion 20 of the blood sample so that when the disc member 18 is added to the previously centrifuged blood sample, the disc member 18 sinks to the bottom of the serum portion 20 of the blood sample. Preferably, the specific gravity of the disc member 18 is greater than about 1.02 and more preferably between about 1.09 and 1.3 so that the disc member 18 is preferably positioned along or in the equilibrium layer of gel material 16 in the serum separator tube 10. The preferred specific gravity of the disc member 18 is about 1.2, so that the disc member 18 may contact or become imbedded in the gel layer 16.

Figure 1:
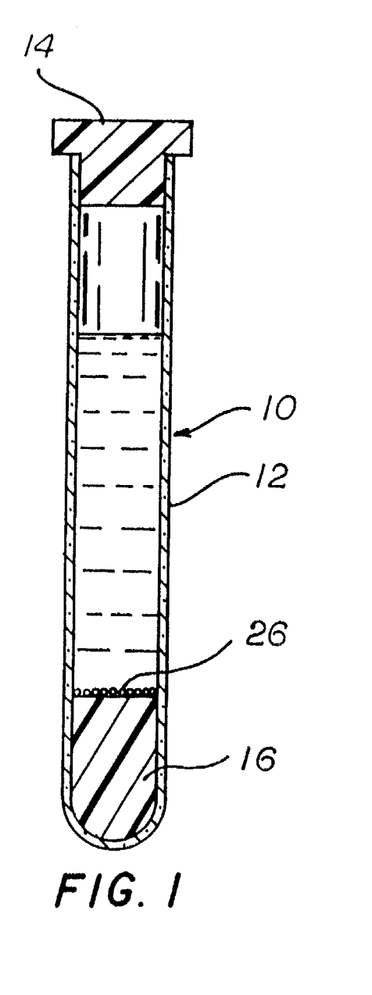
FIG. 1 is a cross-sectional view showing a gel material and blood sample contained in a collection tube prior to centrifugation with the amount of separated oil in the collection tube being exaggerated along the top surface of the gel material.
Figure 2:
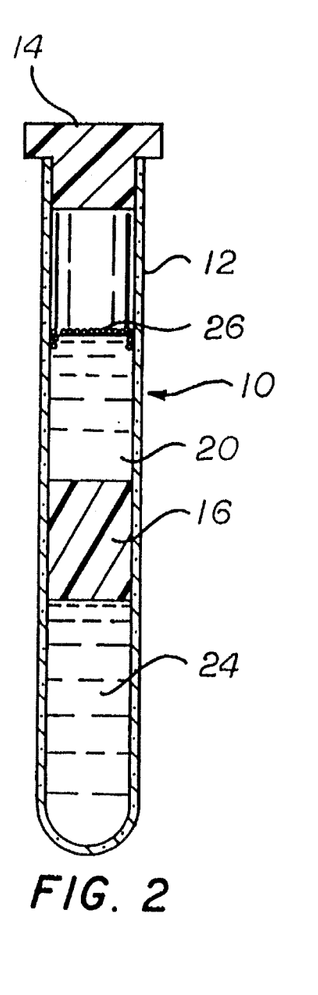
FIG. 2 is a cross-sectional view showing the gel material and blood sample of FIG. 1 after centrifugation wherein the exaggerated separated oil, serum portion, gel material and coagulum are identifiable as separate layers in the collection tube.
Figure 3:
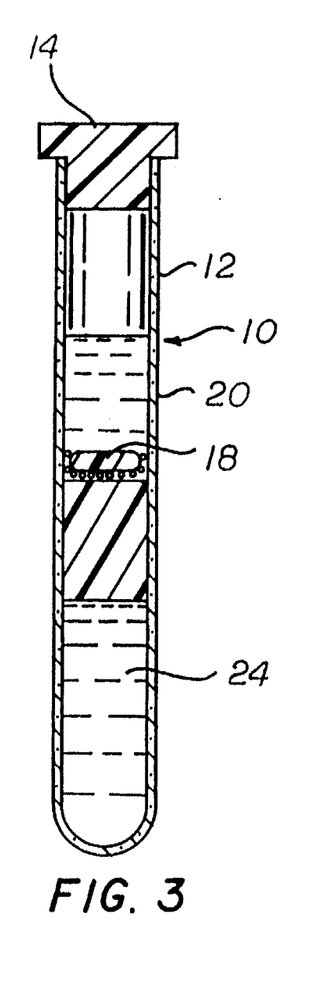
FIG. 3 is a cross-sectional view showing the disc member of the present invention after being dropped into the collection tube of FIG. 2 and further showing the separated oil between the bottom surface of the disc member and the gel layer.
Figure 4:
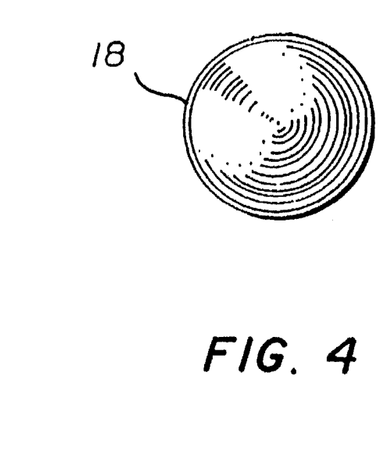
FIG. 4 is an enlarged top view of the disc member of the preferred embodiment.
Figure 5:
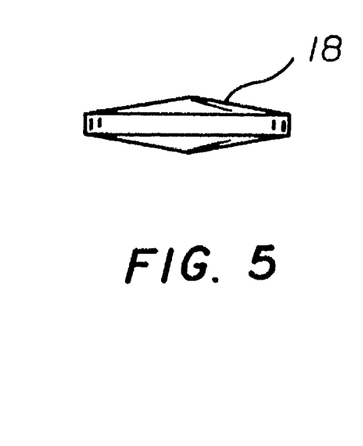
FIG. 5 is an enlarged side view of the preferred form of the disc member.
Figure 6:
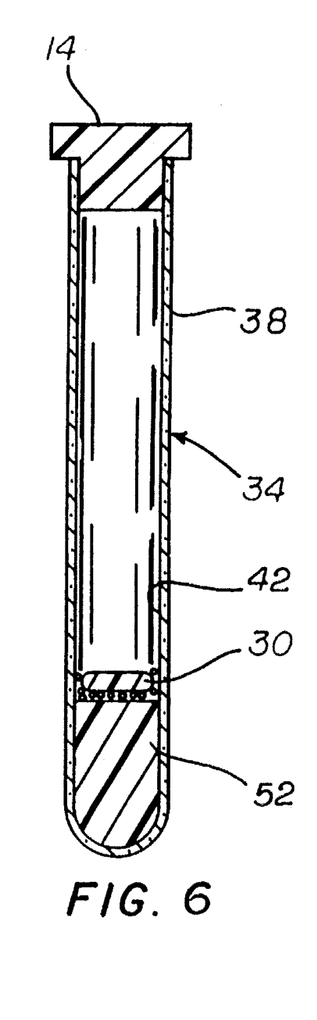
FIG. 6 is a cross-sectional view of the second embodiment of the present invention showing the disc member and gel material in the collection tube prior to the addition of a blood sample and the centrifugation thereof.

In the preferred form of the present invention, it has been found that a disc member 18 having a diamond or oval shape is preferred. For example, when a 16 mm collection tube 12 is used, the disc member 18 preferably has diameter of approximately 0.5 inches and a thickness of approximately 0.15 inches at the center thereof and approximately 0.05 inches around the outer periphery of the disc member 18 as best shown in FIG. 5. With a 13 mm collection tube 12, the disc member 18 preferably has a diameter of approximately 0.383 inches and a thickness of approximately 0.05 inches at the periphery of the disc member 18. With these forms of the preferred embodiment, it has been found that the separated oil 26 adheres to the bottom surface of the disc member 18 as the disc member 18 sinks through the serum portion 20 of the collection tube 12. The diameter of the disc member 18 is chosen so that any separated oil 26 which may be adhering to the sides of the collection tube 12 will be drawn to the disc member 18 while still allowing sufficient space between the periphery of the disc member 18 and the sides of the collection tube 12 to enable the disc member 18 to sink through the serum portion 20 of the blood sample. Additionally, preliminary tests with the disc member 18 of the present embodiment indicate that the specific shape of the disc member 18 is not critical as long as the surface area of the disc member is sufficient to enable all of the separated oil 26 to adhere thereto and the surface of the disc member 18 is hydrophobic and/or non-wetted to attract the separated oil 26 thereto.

With the present embodiment, the blood sample is drawn into the collection tube 12 and coagulation of the blood sample is allowed to occur for a predetermined period of time, e.g. 15 minutes. The collection tube 12 is then centrifuged for a predetermined length of time at a particular centrifugation speed, the particular speed depending on the size of the centrifuge being used. During centrifugation, the coagulum 24 flows downwardly towards the bottom of the tube while the serum portion 20 and gel material 16 flow upwardly along the sides of the collection tube 12. The specific gravity of the gel material 16 is greater than that of the serum portion 20 so that the gel material 16 forms an intermediate layer between the coagulum 24 which includes the portions of the blood sample such as fibrin and red blood cells and the serum portion 20 which is sampled for various tests such as the measurement of certain enzymes and blood glucose. Additionally, because the specific gravity of the separated oil 26 is less than that of the serum portion 20, the separated oil 26 continues to flow upwardly along the sides of the collection tube 12 to the top of the serum portion 20. Further centrifugation of the collection tube 12 causes the separated oil 26 to form a top layer which may cover the serum portion 20 of the blood sample.

With the present embodiment, once the centrifugation is completed, the technician removes the stopper 14 from the open end of the collection tube 12 and manually drops the disc member 18 into the serum separator tube 10. Because the disc member 18 is preferably constructed of a hydrophobic and/or non-wetted material, the layer of the separated oil 26 will adhere to the hydrophobic disc member 18. Any separated oil 26 present in the serum portion 20 of the blood sample will also be removed from the serum portion 20 of the blood sample as the disc member 18 sinks to the layer of gel material 16 in the previously centrifuged serum separator tube 10. Thereafter, the serum separator tube 10 may be inserted into an automated sampling instrument whereupon the probe member may be lowered to the serum portion 20 of the blood sample and an oil-free serum sample may be obtained.

As illustrated in FIGS. 6–13, the second embodiment of the present invention is directed to the use of a disc member 30 having a specific gravity less than about 1.03 and more preferably between about 0.9 and 1.02. As described briefly above, the disc member 30 of the present embodiment is preferably shaped similar to that of the disc member 18 of the preferred embodiment shown in FIGS. 4 and 5. Alternately, the disc member 30 of the present embodiment may be a ring-shaped member 32 as shown in FIGS. 9–13. In this second embodiment, it has been found that the shape of the disc member 30 is more important in the present embodiment than in the prior embodiment because the disc member 30 is located in the serum separator tube 34 prior to the introduction of the blood sample and the red blood cells and fibrin from the blood sample may adhere to the disc member 30 during centrifugation. Although this is believed to be primarily a matter of aesthetic concern, the presence of red blood cells or fibrin on the disc member 30 may affect the tests results from the serum sampling. It has been found that the following form of this embodiment effectively minimizes the adhesion of red blood cells and fibrin on the disc member 30 as described more fully hereinafter.

Figure 7:
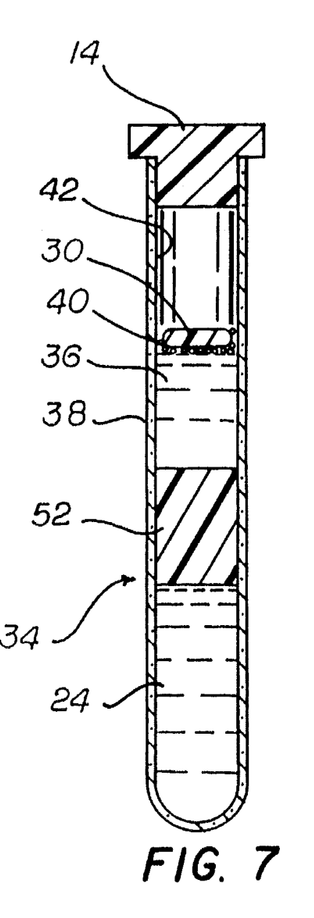
FIG. 7 is a cross-sectional view of the embodiment shown in FIG. 6 wherein the disc member is positioned at the top surface of the serum portion of the centrifuged blood sample.

As shown in FIG. 7, the disc member 30 of this second embodiment is preferably a mirror image disc member with angled top and bottom surfaces of five degrees or more to allow the red blood cells to slide off the disc member 30 during centrifugation. The preferred angle of the top and bottom surfaces of the disc member 30 is between about 7.5 to 12.5 degrees and more preferably approximately 10 degrees. In one form of this embodiment, the outer surface of the disc member 30 is preferably coated with a surfactant such as the commercially available copolymer sold under the trademark DC-190 from Dow Corning Company of Midland, Mich. This water-miscible silicone surfactant may be generally characterized as a silicone-glycol copolymer. Additionally, the red blood cell or fibrin adhesion may be minimized by insuring that the outer surface of the disc member is as smooth as possible. This may be accomplished by polishing the molds for the disc member 30.

Figure 8:
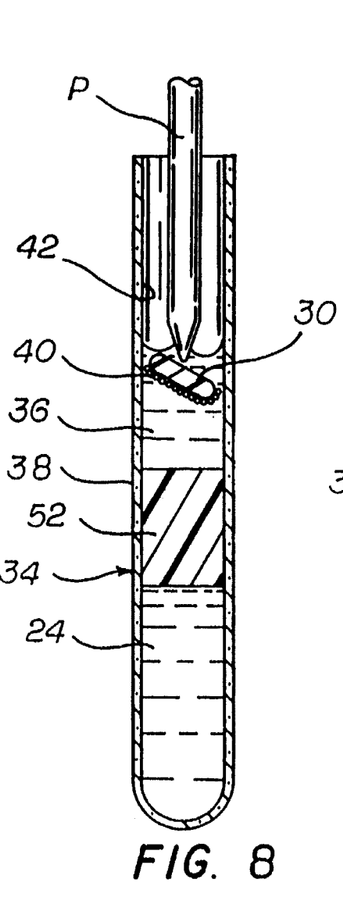
FIG. 8 is a partial cross-sectional view showing a portion of the probe member of an automated sampling instrument contacting the top surface of the disc member to obtain a sample of the serum portion of the blood sample.

The angled or tapered top surface of the disc member 30 serves two important functions during the operation of the present invention. First, the tapered top surface of the disc member 30 does not create false serum contact signals with the air pressure gradient type of auto-sampling instrument. With this type of instrument, as the probe member P moves downwardly in the serum separator tube 34, the probe member P will initially contact the tapered top surface of the disc member 30. Preliminary testing indicates that this contact does not create a false serum contact signal because the probe member P is not contacting a flat surface similar to the top surface of the serum portion 36 of the blood sample. The continued downward movement of the probe member P causes the probe member P to push the disc member 30 out of the way to expose the distal end of the probe member P to the oil-free serum portion 36 of the blood sample as shown in FIG. 8.

The second function of the tapered top surface of the disc member 30 is to provide an oil and red blood cell free surface for contact with the probe member P. As described briefly above, the red blood cells and fibrin slide off the tapered top surface of the disc member 30 during centrifugation. Additionally, the separated oil 40 adheres to and collects along the bottom surface of the disc member 30 in this embodiment. Therefore, the top surface of the disc member 30 is relatively free of contaminants so that serum contact signals are not inhibited with the probe members which use an electrical current to detect the serum portion 36 of the blood sample. Finally, any separated oil 40 which is positioned between the side walls 42 of the collection tube 38 and the disc member 30 will either move downwardly with the disc member 30 as the probe member P moves the disc member 30 downwardly in the collection tube 38 or the separated oil 40 will adhere to the side walls 42 of the collection tube 36. In either situation, the separated oil 40 will not affect the operation of the probe member P.

Figure 13:
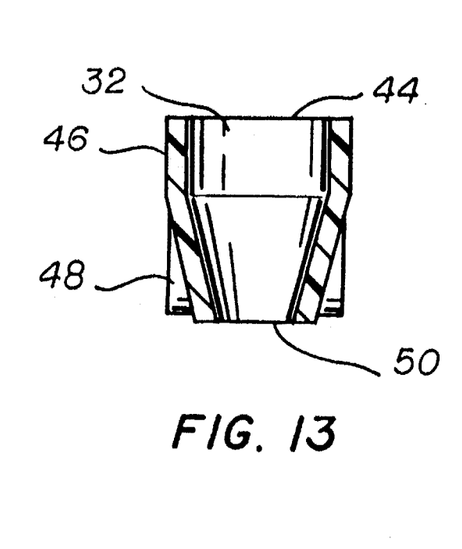
FIG. 13 is an enlarged cross-sectional side view of the ring member taken generally along lines 13—13 of FIG. 12.

The second form of this embodiment is a generally ring-shaped member 32. As shown in FIGS. 9–13, the ring member 32 preferably has an outer diameter of about 0.505 inches and an inner diameter of about 0.440 inches near the top surface 44 thereof and a height of about 0.4 inches when the ring member 32 is used in a 16 mm collection tube. As with the disc member 30 of this embodiment, the ring member 32 is also preferably immersed and coated in a solution of DC-190 to decrease the likelihood that red blood cells will adhere to the ring member 32. The ring member 32 of this embodiment preferably includes a top surface 44 having an outer ring surface 46 which extends downwardly approximately 0.15 inches along the outer periphery of the ring member 32 as shown in FIG. 13. Additionally, the ring member 32 includes a plurality of spaced apart stabilizing fins 48 extending downwardly between the ring surface 46 and the bottom surface 50 of the ring member 32 to prevent the ring member 32 from tilting or otherwise becoming disoriented during centrifugation. The bottom surface 50 of the ring member 32 preferably includes an inner diameter of approximately 0.3 inches so that the overall inner diameter of the ring member 32 is preferably a funnel shape so that the separated oil 40 is inhibited from flowing therethrough. Additionally, the outer surface of the ring member 32 may also include a plurality of circumferentially oriented lip or groove members (not shown) to limit the upward travel of the separated oil 40 along the outer surface of the ring member 32 or to form collection areas for the separated oil 40 along the outer surface of the ring member 32.

In this second embodiment of the present invention, the disc member 30 or ring member 32 is preferably inserted into the collection tube 38 during the manufacture of the serum separator tube 34. Next, a blood sample is drawn into the collection tube 38 and coagulation is allowed to occur for a predetermined period of time. Next, the serum separator tube 34 is centrifuged for a predetermined length of time at a particular centrifugation speed. As the serum separator tube 34 is centrifuged, the coagulum of the blood sample will flow downwardly in the collection tube 38 while the gel material 52 and disc member 30 or ring member 32 will flow upwardly in the collection tube 38. As this occurs, the separated oil 40 will also flow upwardly in the collection tube 38 along the sidewalls 42 of the collection tube 38. The preferred funnel shape of the ring member 32 of this embodiments deflects the separated oil 40 toward the sidewall 42 of the collection tube 38 so that the top center surface of the serum portion 36 is substantially oil free. With the ring member 32 of this embodiment, the separated oil 40 is retained between the outer diameter of the ring member 32 and the inner surface of the sidewalls 42 of the collection tube 48 as shown best in FIG. 11.

As described briefly above, with the disc member 30 of this embodiment, the separated oil 40 will flow upwardly along the sidewalls of the collection tube 38 and contact the bottom surface of the disc member 30. Once centrifugation is completed, the separated oil 40 will contact the sidewalls of the collection tube 48 and the bottom surface of the disc member 30. Therefore, as the probe member enters the collection tube 38, the probe member will initially contact the oil-free top surface of the disc member 30 and continued downward movement of the probe member will cause the disc member, 30 to be displaced so that the probe. enters the oil-free serum portion 36 of the blood sample as shown in FIG. 8.

In addition to the disc-shaped and ring-shaped members of this embodiment, it has also been determined that pellets of material such as polypropylene pellets having a specific gravity of about 0.9 will also effectively entrap the separated oil so that the operation of the automated sampling instrument will not be adversely affected by the separated oil. It has been observed that the attraction between the separated oil and the individual pellets causes the separated oil to accumulate around clumps of pellets which are then displaced by the downward movement of the probe member.

In the present embodiment, in order for the disc member 30 or ring member 32 to function as a integral part of the collection tube 38, the preferred device should meet one or more of the following criteria. First, the material the device is made from should not be significantly wetted by the blood. This is because the hydrophobic oil from the gel material 52 will better adhere to hydrophobic surfaces and therefore, a hydrophobic surface is more efficient at attracting and containing the separated oil from a thixotropic gel material 52. Secondly, the device should not have significant red blood cell or fibrin adhesion. Since the device will function at the top surface of the serum portion 36, the device should not cause significant red blood cell contamination in the serum portion 36 of the blood sample. The presence of red blood cells on the device is aesthetically unpleasing and may cause errors in certain test results. Third, the density of the device should be less than about 1.02 so that the device will float at the top surface of the serum portion 36. Fourth, the device should not become trapped in the blood clot or fibrin during centrifugation, thereby rendering it non-functional. Finally, the shape of the device should be such that the serum portion detection mechanism for the probe member will not be falsely triggered or adversely affected by the device as the probe member is lowered into the serum portion 36 of the blood sample.

Figure 9:
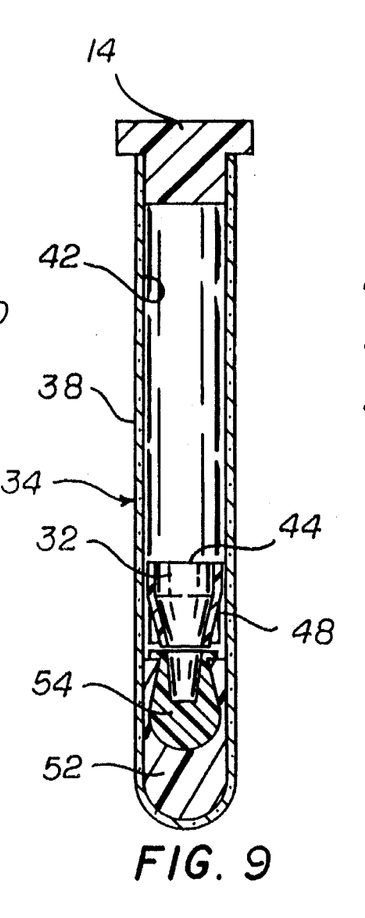
FIG. 9 is a partial cross-sectional view of the embodiment shown in FIG. 6 with a ring-shaped member inserted in the collection tube prior to the addition of the blood sample and the centrifugation thereof.
Figure 10:
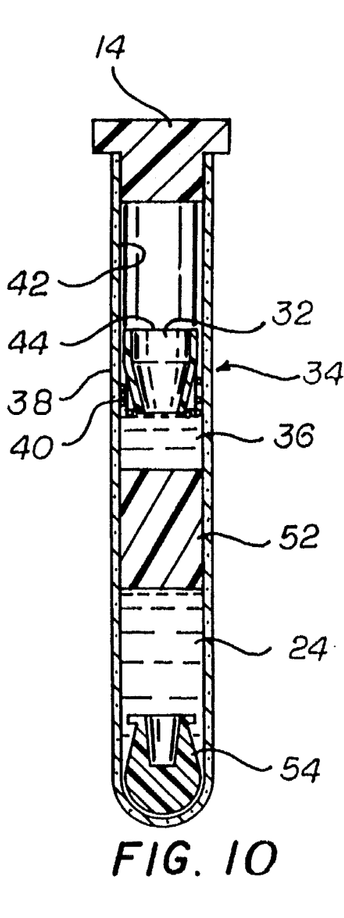
FIG. 10 is a cross-sectional view similar to that of FIG. 7 wherein the ring member is positioned along the top surface of the serum portion of the separated blood sample.
Figure 11:
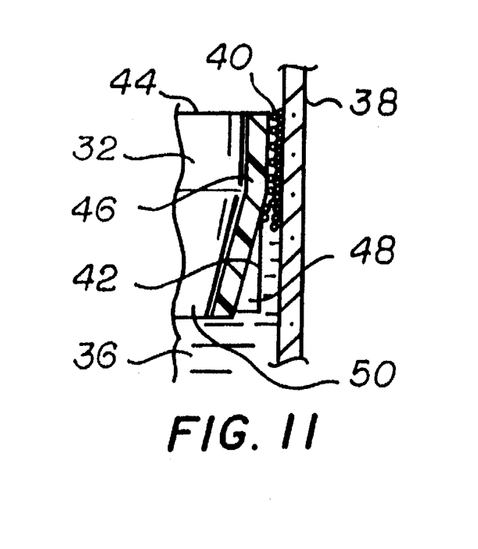
FIG. 11 is an enlarged partial cross-sectional view schematically showing the exaggerated amount of separated oil positioned between the ring member and the side wall of the collection tube as shown in FIG. 10.
Figure 12:
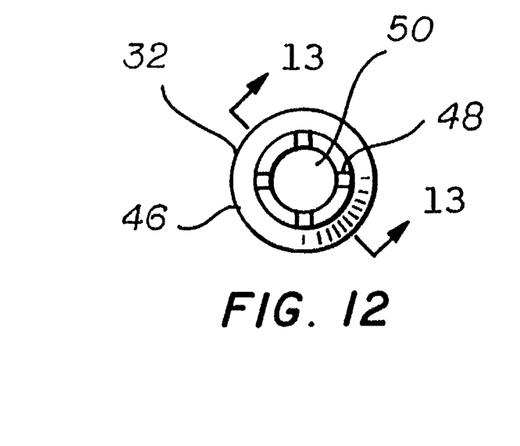
FIG. 12 is a bottom end view of the ring member shown in FIGS. 9–11.

FIGS. 9 and 10 also illustrate the use of an energizer member 54 in combination with the ring member 32. The energizer member 54 is preferably of the type disclosed in U.S. Pat. No. 3,981,804 granted to Gigliello, the disclosure of which is incorporated herein by reference. Although the energizer member 54 is shown in combination with the ring member 32, the energizer member 54 may also be used with the disc member 30 or the other embodiments described herein. The energizer member serves two important functions. First, as briefly described above, the energizer member 54 increases the rate of flow of the gel material 52 from the bottom of the collection tube 38 to the equilibrium level. Additionally, the energizer member 54 causes the disc member 30 or ring member 32 to be spaced apart from the top surface of the gel material 52 during storage. Without the energizer member 54, it is possible that some of the gel material 52 may adhere to the bottom surface of the disc member 30 or ring member 32 so that after centrifugation, some of the gel material 52 may remain on the disc member 30 or ring member 32 and either prevent the disc member 30 or ring member 32 from reaching top surface of the serum portion 36; cause contamination of the serum sample or be drawn into the serum sample by the probe member P. Additionally, during manipulation or other movement of the collection tube 38, it is possible for the disc member 30 to become inverted in the collection tube 38 and therefore, the surface of the disc member 30 having the gel material 52 thereon may become the top surface of the disc member 30 which would then be contacted by the probe member P of the automatic sampling equipment. As described in the Gigliello patent, the energizer member 54 preferably has a specific gravity greater than the gel material 52 so that the energizer member 54 will sink to the bottom of the collection tube 38 after centrifugation as shown in FIG. 10.

Another embodiment of the present invention involves the creation of a hydrophobic surface on the inner walls of the collection tube by washing the surface with a silicone emulsion such as DC-365, a commercially available silicone-water emulsion sold under the trademark DC-365 from Dow Corning Company of Midland, Mich. The silicone emulsion is then adhered to the walls of the collection tube by heating the coated collection tube at temperatures of about 250 degrees for about 2 hours: 275 degrees for about 1 hour or 300 degrees for about 30 minutes. The presence of the silicone emulsion on the walls of the collection tube causes the separated oil to adhere to the sidewalls of the separator tube. Therefore, the center portion of the serum sample remains oil-free and an adequate serum sample may be obtained by using an automated sampling instrument.

FIGS. 14–22 illustrate two further preferred forms of the present invention. FIGS. 14–18 illustrate a device 60 which consists of an upper ring-shaped portion 62 and a lower disc-shaped portion 64. This device 60 is preferably constructed of or coated with a hydrophobic material and has a preferred specific gravity less than about 1.02 and more preferably between about 0.9 and 1.1 so that the device floats above the equilibrium layer of the gel material and in the serum portion of the serum separator tube as described more fully below. The ring-shaped portion 62 of this device 60 is preferably connected to the top surface 66 of the disc-shaped portion 64 by a pair of downwardly extending and tapered support members 68 and 70. When this embodiment is used in a 16 mm collection tube as described above, the device 60 is preferably about 0.44 inches long and the outer preferred outer diameter at the top of the ring-shaped portion 62 is about 0.45 inches and the inner diameter of the top of the ring-shaped portion 62 is about 0.43 inches.

Figure 14:
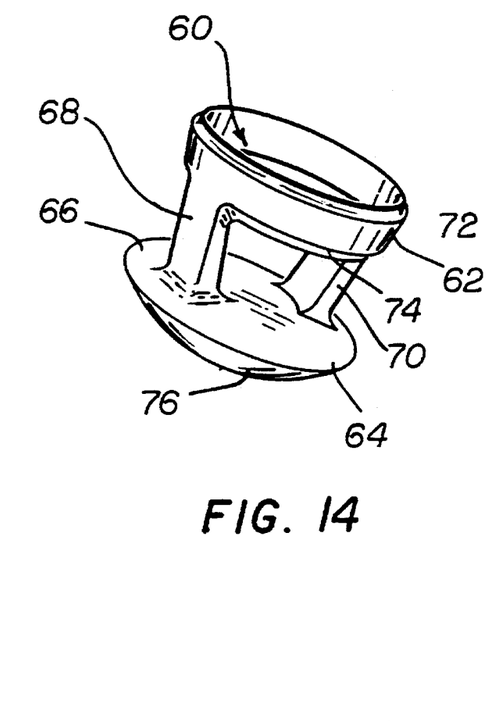
FIG. 14 is a perspective view of an alternate embodiment of the present invention which is preferably used in a collection tube of the type shown in FIGS. 1–3 and 6–10.
Figure 15:
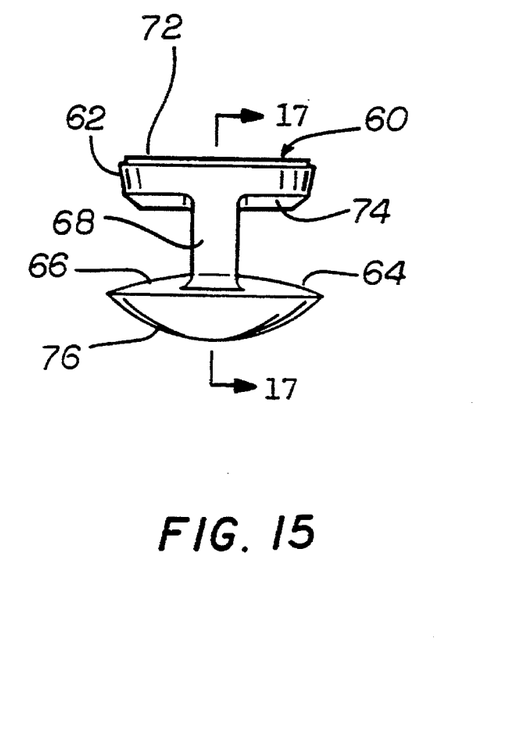
FIGS. 15 and 16 are side views of the embodiment the present invention shown in FIG. 14.
Figure 16:
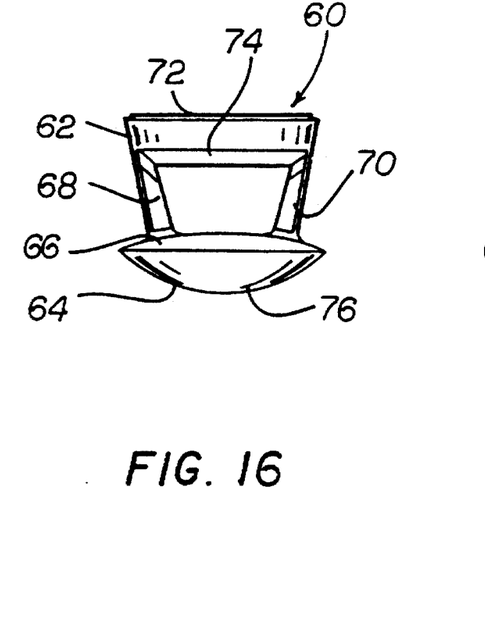
Figure 17:
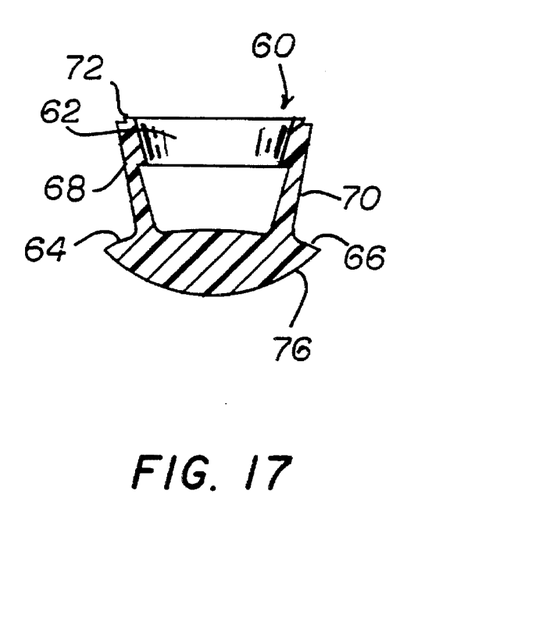
FIG. 17 is a cross-sectional view of the embodiment shown in FIG. 14 taken generally along lines 17—17 of FIG. 15.

As best shown in FIG. 17, the top surface of the ring-shaped portion 62 preferably has a larger diameter than the bottom surface thereof and includes a lip member 72 extending upwardly therefrom to form an extension along the inner diameter of the ring-shaped portion 62. As best shown in FIGS. 14 and 16, the bottom surface of the ring-shaped portion 62 preferably includes a chamfered surface 74 thereon. The ring-shaped portion 62 is preferably about 0.1 inch high and the support members 68 and 70 are preferably about 0.25 inches long when the device 60 of the present invention is used in a 16 mm collection tube. The support members 68 and 70 preferably taper outwardly from the top surface 66 of the disc-shaped portion 64 at a preferred angle of about 75 to 80 degrees between the top surface 66 of the disc-shaped portion 64 and the ring-shaped portion 62 of the device 60.

The disc-shaped portion 64 of this device 60 preferably has an outer diameter of about 0.44 inches which is preferably intermediate to the inner and outer diameter of the top surface of the ring-shaped portion 62 and a thickness of about 0.14 inches at the center thereof when this member 60 is used in a 16 mm collection tube. Unlike the disc member 30 described above, the disc-shaped portion 64 of the present embodiment preferably does not have mirror image top and bottom surfaces. In this embodiment, the bottom surface 76 of the disc-shaped portion 64 has a spherical shape with a radius which is approximately one-half of the radius of the spherically-shaped top surface 66. For example, when the disc-shaped portion 64 is used in a 16 mm collection tube, the bottom surface 76 has a preferred radius of about 0.375 inches and the top surface 66 has a radius of about 0.75 inches.

The shape of device 60 is believed to inhibit the travel of the separated oil towards the top of the serum portion of the blood sample as the separated oil travels along the sides of the collection tube and also along the top surface of the serum portion of the blood sample. As described above, during centrifugation, the separated oil initially travels upwardly along the sides of the collection tube. When the separated oil reaches the top surface of the serum portion, the separated oil then travels inwardly to form a layer of separated oil along the top surface of the separated blood sample.

Figure 18:
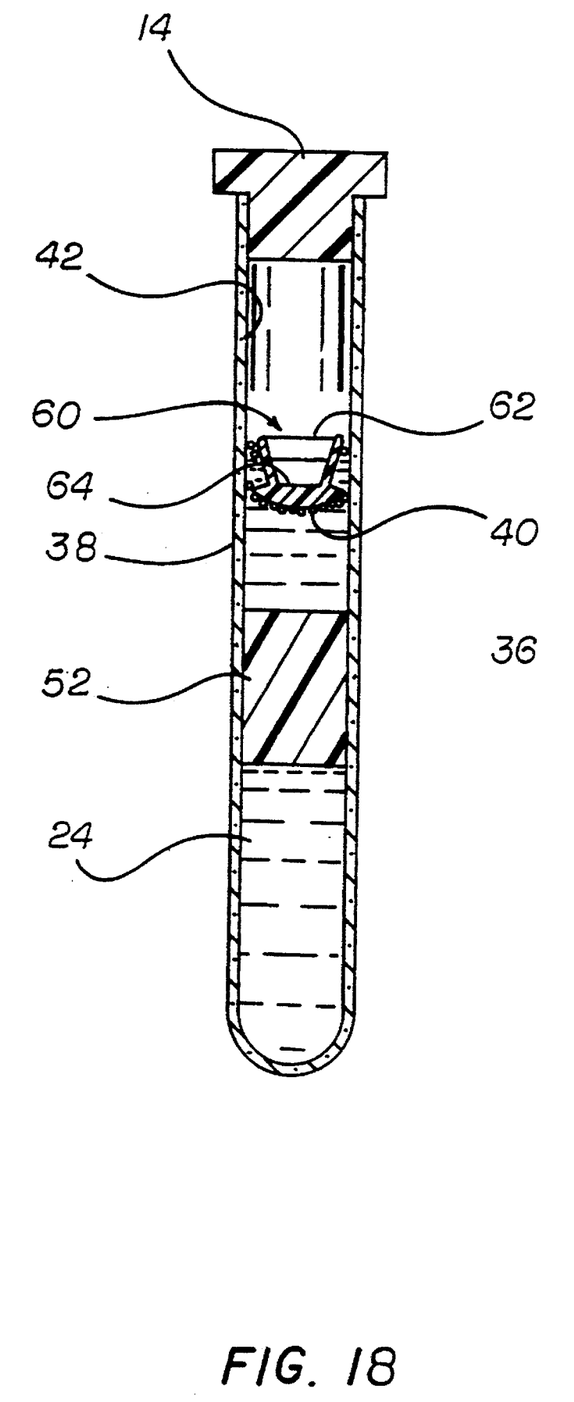
FIG. 18 is a cross-sectional view of the embodiment shown in FIG. 14 wherein the device of this embodiment is positioned in the serum portion of the centrifuged blood sample showing the exaggerated amount of separated oil therein.
Figure 19:
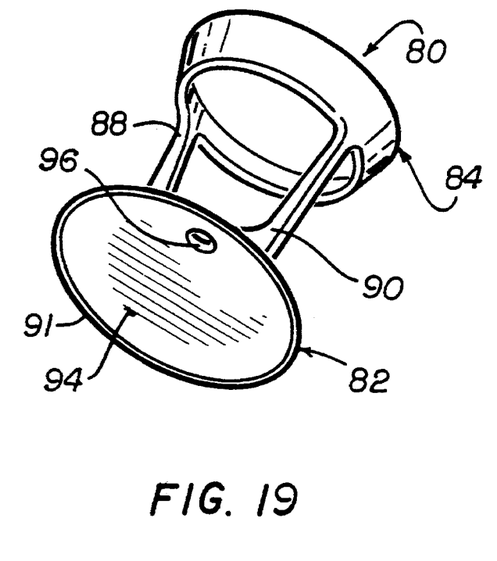
FIG. 19 is a perspective view of a further alternate embodiment of the present invention which is preferably used in a collection tube of the type shown in FIGS. 1–3 and 6–10.
Figure 20:
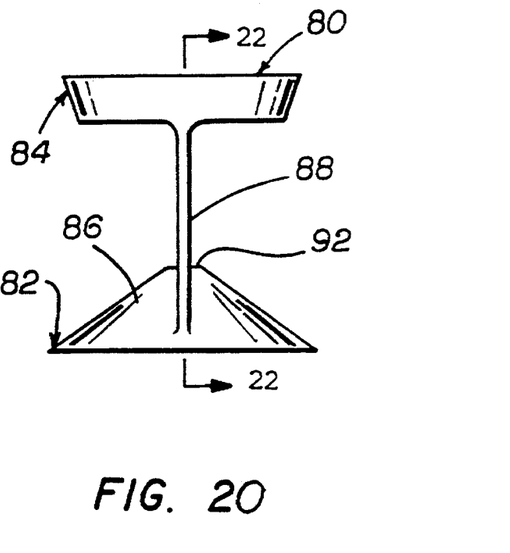
FIGS. 20 and 21 are side views of the embodiment of the present invention shown in FIG. 19.

The device 60 shown in FIGS. 14–18 is preferably inserted into a collection tube of the type described above after the blood sample containing serum separator tube has been centrifuged. Because the specific gravity of this device 60 is less than the specific gravity of the gel material and preferably less than the specific gravity of the serum portion of the blood sample, the device 60 will float in the serum portion of the blood sample as described above with respect to the second embodiment of the present invention. Additionally, as shown in FIG. 18, the top portion of the ring-shaped portion 62 of this device 60 is preferably positioned above the top surface of the serum portion to physically prevent the separated oil from flowing toward the center of the top surface of the serum portion.

As the device 60 is dropped into the separated blood sample, the separated oil will initially contact the bottom surface 76 of the disc-shaped portion 64 of the device 60. Preliminary testing has shown that the majority of the separated oil will adhere to the bottom surface 76 of the disc-shaped portion 64 and therefore in the present embodiment, the bottom surface 76 of the disc-shaped portion 64 has been designed to have a greater surface area than the top surface 66 of the disc-shaped portion 64. Additionally, the bottom surface 76 of the disc-shaped portion 64 has also been found to effectively prevent the trapping of air bubbles along the bottom surface 76 or the outer diameter of the disc-shaped portion 64. The outer diameter of the disc-shaped portion 64 is preferably less than or equal to the maximum outer diameter of the ring-shaped portion 62 to increase the ability of the device 60 to sink in the serum portion of the blood sample while retaining a relatively large surface area for contact with the separated oil. The chamfered surface 74 on the bottom surface of the ring-shaped portion 62 functions to decrease the surface tension of the serum portion to facilitate the sinking of the device 60 into the serum portion and also directs any separated oil which has not adhered to the bottom surface 76 or top surface 66 of the disc-shaped portion 64 outwardly towards the walls of the collection tube and along the outer surface of the ring-shaped portion 62. Finally, as shown in FIG. 18, the lip member 72 functions to retain the separated oil along the walls of the collection tube by preventing the separated oil from flowing towards the center of the collection tube and thereby interfering with the probe member of the sampling instrument.

Figure 21:
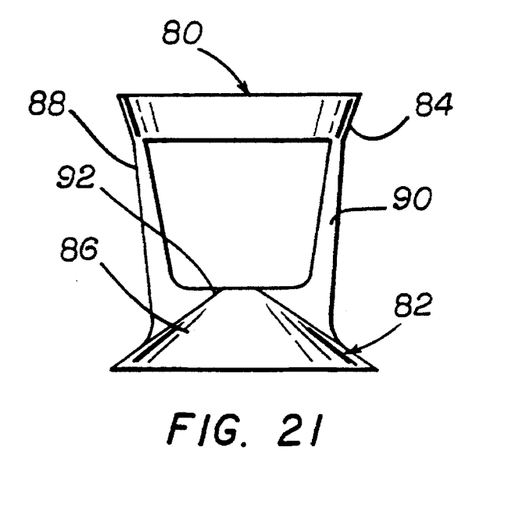
Figure 22:
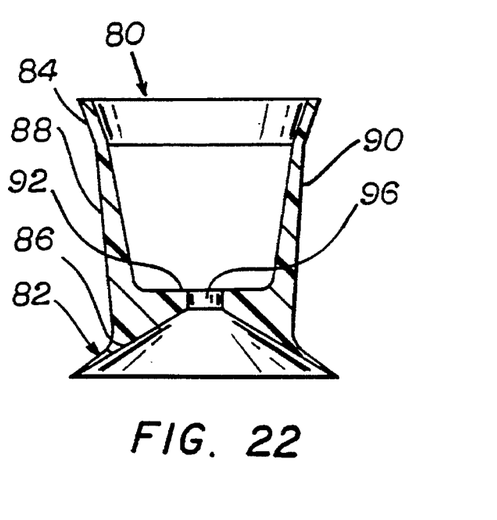
FIG. 22 is a cross-sectional view of the embodiment shown in FIG. 19 taken generally along lines 22—22 of FIG. 20.

FIGS. 19–22 illustrate another form of the present embodiment wherein the disc-shaped portion 64 of the device 60 described above is replaced with a funnel-shaped member 82. The device 80 shown in FIGS. 19–22 consists of a lower funnel-shaped member 82 and an upper ring-shaped portion 84. The ring-shaped portion 84 of this device 80 is preferably connected to the top surface 86 of the funnel-shaped member 82 by a pair of downwardly extending and tapered support members 88 and 90. When this embodiment is used in a 16 mm collection tube as described above, the device is preferably about 0.5 inches high and the preferred outer diameter at the top of the ring-shaped portion 84 is about 0.44 inches. The preferred outer diameter of the device 80 at the bottom of the funnel-shaped member 82 is about 0.44 inches. As best shown in FIG. 22, the ring-shaped portion 84 tapers outwardly from the top of the support members 88 and 90 and is approximately 0.08 inches high. The support members 88 and 90 are preferably about 0.27 inches high and taper from the ring-shaped portion 84 to the funnel-shaped member 82.

The funnel-shaped member 82 of this device 80 is preferably conically shaped and has a height of about 0.15 inches. The funnel-shaped member 82 preferably includes a bottom base surface 91 and a top apex area 92. The apex area 92 preferably includes a centrally positioned opening 96 through the top surface 86 thereof. The opening 94 preferably has a diameter of about 0.06 inches so that air is allowed to flow therethrough when the device 80 is initially dropped into the collection tube. As shown in FIG. 21, the funnel-shaped member 82 is preferably thicker near the apex area 92 than near the base surface 91.

The device 80 shown in FIGS. 18–22 is preferably inserted into a collection tube of the type described above after the blood sample containing serum separator tube has been centrifuged. Because the specific gravity of this device 80 is similar to the specific gravity of the device 60, the device 80 will float in the serum portion of the blood sample as described above with respect to device 60. As the device 80 is dropped into the separated blood sample, any air trapped along the bottom surface 94 of the funnel-shaped member 82 will flow through the opening 96. Preliminary testing has shown that the separated oil will be trapped along the bottom surface 94 of the funnel-shaped member 82 and the opening will usually become blocked by an air bubble or by to the surface tension of the separated oil as the device 80 sinks in the serum portion of the separated blood sample. Therefore, the funnel-shaped member 82 effectively functions to remove the majority of the separated oil from the top surface of the serum portion. Any separated oil which is not trapped along the bottom surface 94 of the funnel-shaped portion 82 will flow along the side walls of the collection tube and will adhere to the top surface 86 of the funnel-shaped member 82 or will contact the outer surface of the ring-shaped portion 84. As with the ring-shaped portion of the device 60 described above, the ring-shaped portion 84 of this device 80 preferably floats above the top surface of the serum portion to prevent the separated oil from flowing towards the center of the serum portion by trapping the separated oil between the outer surface of the ring-shaped portion 84 and the side walls of the collection tube. Finally, the use of hydrophobic materials and/or a hydrophobic coating on the device 80 will cause the separated oil to adhere to the device 80 so that the separated oil does not interfere with the operation of the probe member.

Although the devices 60 and 80 are described above as being inserted into the serum separator tube after centrifugation of the blood sample, it is believed that the devices 60 and 80 may also be placed in the serum separator tube during the manufacture thereof without substantial modification to the device 60 or 80 and the operation of these devices 60 or 80 would be similar to the operation of the ring member 32 as described above. For example, it is believed that device 80 as described above would function satisfactorily if used in this manner by removing the opening 96 from the funnel-shaped member 82. These device 60 or 80 may also be used with an energizer member 54 of the type described above and shown in FIGS. 9 and 10 so that the device does not become trapped in the gel material during centrifugation.

In the present invention, the above described disc members, ring members and combinations thereof are preferably constructed of a hydrophobic and/or non-wetted materials such as polypropylene, polyethylene or a 40% talc filled polypropylene. It is anticipated that nearly any material may be used as long as the material has an affinity for the separated oil or other degradation material that has separated from the gel material and/or the shape of the device is such that the separated oil or other degradation material is physically prevented from interfering with the operation of the probe member. Therefore, the preferred material of the above described embodiments is related to the type of degradation material which has separated from the gel material. Finally, the preferred material should not significantly affect the composition of the serum portion of the blood sample so that the test results obtained with this device are not altered.

The foregoing description of the various embodiments of the present invention is intended to be illustrative of the various preferred forms of the present invention. The shapes, sizes and preferred materials described above are intended to be for illustrative purposes only and are not intended to limit the scope of the present invention in any way. The scope of the present invention is intended to be defined by the following claims.

What is claimed is:

1. A method for preventing the degradation material of a barrier material from interfering with the sampling of a portion of a separated portion of a blood sample in a container wherein the blood sample has at least a lighter phase and a heavier phase and the specific gravity of the heavier phase is greater than the specific gravity of the lighter phase, the method including:

inserting a blood sample into a container having a bottom end and an open end with a stopper member thereon and a barrier material therein, wherein the barrier material includes a degradation material which separates therefrom, and the barrier material has a specific gravity between the specific gravities of the heavier phase and the lighter phase of the blood sample;

centrifuging the container to separate the heavier and lighter phases of the blood sample such that the barrier material forms a mechanical barrier between the heavier and lighter phases of the blood sample;

inserting a device member into the container to physically separate the degradation material from the lighter phase to enable a sample of the lighter phase of the blood sample to be obtained from the container such that the sample of the lighter phase is not contaminated by the degradation material; and wherein the device member floats in the lighter phase of the blood sample.

2. A method for preventing the degradation material of a barrier material from interfering with the sampling of a portion of a separated portion of a blood sample in a container wherein the blood sample has at least a lighter phase and a heavier phase and the specific gravity of the heavier phase is greater than the specific gravity of the lighter phase, the method including:

inserting a blood sample into a container having a bottom end and an open end with a stopper member thereon and a barrier material therein, wherein the barrier material includes a degradation material which separates therefrom, and the barrier material has a Specific gravity between the specific gravities of the heavier phase and the lighter phase of the blood sample;

centrifuging the container to separate the heavier and lighter phases of the blood sample such that the barrier material forms a mechanical barrier between the heavier and lighter phases of the blood sample;

inserting a device member into the container to physically separate the degradation material from the lighter phase to enable a sample of the lighter phase of the blood sample to be obtained from the container such that the sample of the lighter phase is not contaminated by the degradation material; and wherein said device member has a specific gravity less than the specific gravity of the barrier material.

3. The method of claim 2 wherein the degradation material has an affinity for said device means such that the degradation material adheres thereto as said device member sinks in the lighter phase.

4. The method of claim 2 wherein centrifugation of the container causes a portion of the device member to float above the top surface of the lighter phase.

5. A method for preventing the degradation material of a barrier material from interfering with the sampling of a portion of a separated portion of a blood sample in a container wherein the blood sample has at least a lighter phase and a heavier phase and the specific gravity of the heavier phase is greater than the specific gravity of the lighter phase, the method including:

inserting a blood sample into a container having a bottom end and an open end with a stopper member thereon and a device member and barrier material therein, wherein the barrier material includes a degradation material which separates therefrom, and the barrier material has a specific gravity between the specific gravities of the heavier phase and the lighter phase of the blood sample and the device member has a specific gravity less than the specific gravity of the barrier material; and centrifuging the container to separate the heavier and lighter phases of the blood sample such that the barrier material forms a mechanical barrier between the heavier and lighter phases of the blood sample and the device member physically separates the degradation material from the barrier material and the lighter phase of the blood sample to enable a sample of the lighter phase to be obtained from the container such that the sample of the lighter phase is not contaminated by the degradation material.

6. The method of claim 5 wherein the device member floats in the lighter phase of the fluid sample.

7. The method of claim 5 wherein the degradation material has an affinity for said device member such that the degradation material adheres thereto.

8. The method of claim 5 wherein centrifugation of the container causes the device member to float towards the top surface of the lighter phase.

9. The method of claim 8 wherein a portion of the device member extends above the top surface of the lighter phase after centrifugation.

10. A method for preventing a degradation material which separates from a barrier material from interfering with the sampling of a portion of a separated portion of a blood sample in a collection tube wherein the blood sample has at least a lighter phase and a heavier phase, and the specific gravity of the heavier phase is greater than the specific gravity of the lighter phase, the method including:

inserting a blood sample into a blood collection tube having a bottom end and an open end with a stopper member thereon and a barrier material therein, wherein the barrier material has a specific gravity between the specific gravities of the heavier phase and the lighter phase;

centrifuging the blood collection tube to separate the heavier and lighter phases of the blood sample such that the barrier material forms a mechanical barrier between the heavier and lighter phases of the blood sample;

inserting a device member into the blood collection tube to physically separate the degradation material from the barrier material and the lighter phase of the blood sample to enable a sample of the lighter phase of the blood sample to be obtained from the blood collection tube which is not contaminated by the degradation material from the barrier material; and wherein the device member floats in the lighter phase of the blood sample.

11. A method for preventing a degradation material which separates from a barrier material from interfering with the sampling of a portion of a separated portion of a blood sample in a collection tube wherein the blood sample has at least a lighter phase and a heavier phase, and the specific gravity of the heavier phase is greater than the specific gravity of the lighter phase, the method including:

inserting a blood sample into a blood collection tube having a bottom end and an open end with a stopper member thereon and a barrier material therein, wherein the barrier material has a specific gravity between the specific gravities of the heavier phase and the lighter phase;

centrifuging the blood collection tube to separate the heavier and lighter phases of the blood sample such that the barrier material forms a mechanical barrier between the heavier and lighter phases of the blood sample;

inserting a device member into the blood collection tube to physically separate the degradation material from the barrier material and the lighter phase of the blood sample to enable a sample of the lighter phase of the blood sample to be obtained from the blood collection tube which is not contaminated by the degradation material from the barrier material; and wherein said device member has a specific gravity less than the specific gravity of the barrier material.

12. The method of claim 11 wherein the device is inserted into the blood collection tube prior to the insertion of the blood sample therein.

13. The method of claim 11 wherein the device member is inserted into the blood collection tube after the blood sample is inserted into the blood collection tube.

14. The method of claim 11 wherein the separated material has an affinity for the device member such that the separated material is attracted thereto.

* * * * *